United States Patent [19]
Nixon et al.

[11] Patent Number: 5,985,581
[45] Date of Patent: Nov. 16, 1999

[54] USE OF PRESENILIN-1 FOR DIAGNOSIS OF ALZHEIMERS DISEASE

[75] Inventors: Ralph A. Nixon, Tarrytown; Anne M. Cataldo, Nanuet; Benjamin H. Kao, New York; Paul M. Mathews, Irvington, all of N.Y.

[73] Assignee: The McLean Hospital Corporation, Belmont, Mass.

[21] Appl. No.: 08/896,176

[22] Filed: Jul. 17, 1997

Related U.S. Application Data

[60] Provisional application No. 60/022,594, Jul. 25, 1996.

[51] Int. Cl.$^6$ .......................... G01N 33/53; G01N 33/48; G01N 33/543
[52] U.S. Cl. ........................ 435/7.1; 435/7.92; 436/63; 436/512; 436/518; 436/528; 436/529; 436/530; 436/535; 436/161; 436/547; 436/548; 436/811
[58] Field of Search ...................... 424/9.1, 141.2, 424/145.1, 141.1; 435/7.1, 7.92, 7.94, 70.21; 436/811, 824, 548, 518, 528, 529, 530, 535, 512, 161, 63, 547

[56] References Cited

FOREIGN PATENT DOCUMENTS

WO 95/05604  2/1995  WIPO .
WO 95/11314  4/1995  WIPO .

OTHER PUBLICATIONS

Schellenberg et al., "Genetic Linkage Evidence for a Familial Alzheimer's Disease Locus on Chromosome 14" Science, 258:668, (1992).

Alzheimer's Disease Collaborative Group, "The structure of the presenilin 1 (S182) gene and identification of six novel mutations in early onset AD families" Nature Genet., 11:219, (1995).

Sorbi et al., "Missense mutation of S182 gene in Italian families with early–onset Alzheimer's disease" Lancet, 346:439, (1995).

Van Broeckhoven, "Presenilins and Alzheimer disease" Nature Genet., 11:230, (1995).

Wasco et al., "Familial Alzheimer's chromosome 14 mutations" Nature Med., 1:848, (1995).

Sherrington et al., "Cloning of a gene bearing missense mutations in early–onset familial Alzheimer's disease" Nature, 375:754, (1995).

Levy–Lahad et al., "A Familial Alzheimer's Disease Locus on Chromosome I" Science, 269:970, (1995).

Levy–Lahad et al., "Candidate Gene for the Chromosome 1 Familial Alzheimer's Disease Locus" Science, 269:973, (1995).

Li et al., "Identification and expression analysis of a potential familial Alzheimer disease gene on chromosome 1 related to AD3" Proc. Natl. Acad. Sci. USA, 92:12180, (1995).

Rogaev et al., "Familial Alzheimer's disease in kindreds with missense mutations in a gene on chromosome 1 related to the Alzheimer's disease type 3 gene" Nature, 376:775, (1995).

Kovacs et al., Alzheimer–associated presenilins 1 and 2: Neuronal expression in brain and localization to intracelular membranes in mammalian cells Nature Med., 224:224, (1996).

Moussaoui et al., "Immunohistochemical analysis of presenilin–1 expression in the mouse brain" FEBS Letters, 383:219, (1996).

Pettegrew et al., "The Role of Membranes and Energetics in Alzheimer Disease" Alzheimers Disease, eds. R.D. Terry, R. Katzman, and K.L. Bick, Raven Press, NY, pp. 369–386 (1994).

Harrison, "S182: from worm sperm to Alzheimer's disease" The Lancet, 346:388, (1995).

Schwagerl et al., "Elevated Levels of the Endosomal—Lysosomal Proteinase Cathepsin D in Cerebrospinal Fluid in Alzheimer Disease" Journal of Neurochemistry, 64:443, (1995).

*Primary Examiner*—S. Mark Clardy
*Assistant Examiner*—Michael G. Hartley
*Attorney, Agent, or Firm*—Clark & Elbing, LLP.; Kristina Bieker-Brady

[57] ABSTRACT

The invention provides a method of diagnosing Alzheimer's disease. The method utilizes presenilin-1, whose level is found to be substantially decreased in Alzheimer's patients. Included in the invention are diagnostic kits for Alzheimer's disease and methods of screening for effective therapeutics for the disease. The invention also provides a method of studying the function and regulation of presenilin-1 in brain by the use of primate retinoblastoma cells.

9 Claims, 7 Drawing Sheets

5,985,581

USE OF PRESENILIN-1 FOR DIAGNOSIS OF ALZHEIMERS DISEASE

CROSS REFERENCE TO RELATED APPLICATION

This application claims benefit from provisional application No. 60/022,594, filed Jul. 25, 1996.

BACKGROUND OF THE INVENTION

This invention relates to diagnosis of Alzheimer's disease.

Alzheimer's disease (AD) is a devastating impairment of cognitive function prevalent in individuals generally forty-five or older. The cause of AD is not known, nor is there a treatment for AD. However, AD is the first common disease for which allelic variation or mutations at multiple genetic loci are linked to the development of disease in affected families (Roses, Annu. Rev. Med. 47: 387, 1996; Schellenberg, Proc. Natl. Acad. Sci. USA, 92: 8552, 1995). The majority (70–80%) of heritable, early-onset AD maps to chromosome 14 and appears to result from one of more than 20 different amino-acid substitutions within presenilin-1 (PS1) (Schellenberg et al., Science, 258: 668, 1992; Alzheimer's Disease Collaborative Group, Nature Genet, 11: 219, 1995; Sobi et al., Lancet., 346: 439, 1995; Van Broeckhoven, Nature Genet., 11: 230, 1995; Wasco et al., Nature Med., 1: 848, 1995; Sherrington et al., Nature, 375: 754, 1995), the product of the recently identified S182 gene (Sherrington et al., 1995). A similar, although less common, AD-risk locus on chromosome 1 encodes the highly homologous presenilin-2 (Levy-Lahad et al., Science, 269: 970, 1995; Levy-Lahad et al., Science, 269: 973, 1995; Li et al., Proc. Natl. Acad. Sci. USA, 92: 12180, 1995; Rogaev et al., Nature, 376: 775, 1995). Several amino-acid substitutions have been identified within PS2 that appear to be causative for early-onset AD (Levy-Lahad et al., Science, 269: 973, 1995; Li et al., Proc. Natl. Acad. Sci. USA, 92: 12180, 1995; Rogaev et al., Nature, 376: 775, 1995). Based upon mRNA detection, the presenilins appear to be ubiquitously expressed, suggesting that they are housekeeping proteins required by many cell types.

The two mammalian presenilins share 67% amino-acid identity and apparently belong to a larger gene-family of multimembrane spanning proteins that includes the C. elegans spe-4 and sel-12 genes. Mutations in the spe-4 gene disrupt the formation of a Golgi-derived storage and delivery organelle required for spermatogenesis in the nematode (L'Hernault et al., J. Cell Bio., 119: 55, 1992). SEL-12 has been shown to facilitate signaling by lin-12, a member of the Notch family of transmembrane receptors critical for cell surface to nucleus signaling during development (Levitan et al., Nature, 377: 351, 1995). A possible ER and/or Golgi localization of epitope-tagged constructs overexpressed in cultured cells and a similar immunolabeling pattern reported in mouse pyramidal neurons are consistent with the presenilins being integral membrane proteins found within compartments of the secretory pathway (Kovacs et al., Nature Med., 224: 224, 1996; Moussaoui et al., FEBS Letters, 383: 219, 1996). This, in conjunction with the spe-4 phenotype and the known importance of membrane proteins and their compartmentalization in AD, has led to the conjecture that the presenilins play a role in membrane protein trafficking and/or processing along the secretory pathway (Kovacs et al., Nature Med., 224: 224, 1996; Pellegrew et al., in Alzheimer disease, eds. R. D. Terry, R. Katzman, and K. L. Bick, Raven Press, New York, 1994; Harrison, Lancet, 346: 388, 1995). However, no direct evidence currently exists ascribing such a function to the presenilins, nor is there evidence suggesting any specialized role for presenilins in the brain. Finally, the broad distribution of the identified AD-causing mutations throughout PS1 and PS2 has yet to suggest any clear mechanistic link between these mutations and the disease process (Van Broeckhoven, Nature Genet., 11: 230, 1995).

SUMMARY OF THE INVENTION

We have shown that the amount of presenilin-1 (PS1) is substantially decreased in the ventricular cerebrospinal fluid (CSF) of Alzheimer's patients relative to unaffected individuals. Thus, detection and quantification of PS1 in CSF is useful for diagnosing Alzheimer's disease.

Accordingly, in the first aspect, the invention provides a method for diagnosing AD in a human patient. In this method, the amount of PS1 present in the patient'CSF is determined relative to the amount of PS1 present in a control sample of the same type (e.g., lumbar CSF or ventricular CSF) from an unaffected human. A substantial decrease (see below) of the PS1 level in CSF from the patient relative to the control indicates a diagnosis of Alzheimer's disease.

In the second aspect, the invention provides a method for producing an antibody which specifically recognizes PS1 and its isoforms. Such an antibody enables the use of immunoassays (e.g., Western blot analysis and ELISA) for analyzing the PS1 level in biological samples from patients.

The invention can thus be practiced using a diagnosis kit that includes (1) a primary antibody that specifically binds to PS1, or preferably to PS1's N terminus, and (2) a secondary antibody that is conjugated to a signal-producing label, and is capable of binding to the primary antibody or to a PS1 site different from the site where the primary antibody binds. The signal-producing label linked to the secondary antibody may be, but is not limited to, an enzyme, e.g., horseradish peroxidase or alkaline phosphatase. Preferably, both the enzyme and its substrate are provided in the kit.

In another aspect, the invention features a method for determining the effectiveness of a candidate Alzheimer's therapeutic. In this method, the candidate compound is introduced to Alzheimer's patients, most preferably into the brain tissue. The PS1 level in CSF from these patients is analyzed at multiple time points and a substantial restoration of the PS1 level in these patients indicates the effectiveness of the compound.

In another aspect, the invention features a method for studying the function and regulation of PS1, and ultimately, for understanding Alzheimer's pathogenesis. This method involves the use of a primate retinoblastoma cell line, preferably Y79. Y79 displays a PS1 processing pattern that is characteristic of brain tissue. Thus such a cell line can serve as a model system for brain with respect to PS1's expression and processing. Compounds capable of modulating PS1 expression and processing can also be selected by the use of such a cell line.

As used herein, PS1 means the entire protein encoded by the S182 gene (Sherrington et al., 1995); it also includes all isoforms of PS1.

The "amino terminal region" of PS1, as used herein, refers to the first 100 amino acids starting from the amino terminus.

A clinically indicative "decrease" relative to normal (or control) in the PS1 level, as used herein, means that the total amount of PS1, all isoforms included, is at least 50% or preferably 200% below normal. By "normal" or "control" is meant the biological sample from or the PS1 level of an individual not affected by AD.

By "cerebrospinal fluid" is meant the fluid which surrounds the bulk of the nervous system, as described in *Physiological Basis of Medical Practice* (ed. J. B. West, Williams and Wilkins, Baltimore, Md., 1985). Cerebrospinal fluid includes ventricular and lumbar CSF.

By "immunoassay" is meant any method of detecting proteins or peptides that involves the use of an antibody.

By "primate retinoblastoma cell" lines is meant any cell line that is isolated from a primate (e.g., human) and of a retinoblastoma or related nature.

Other features and advantages of the invention will be apparent from the following detailed description, drawings, and claims.

Figure 1A:
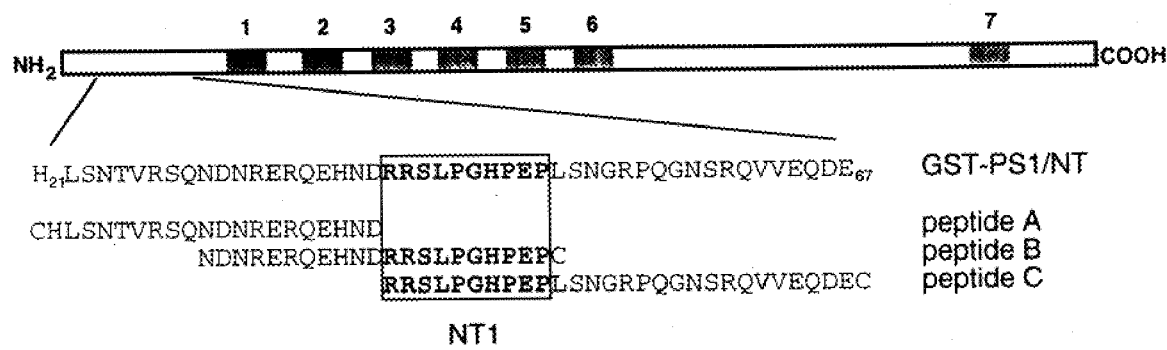
FIG. 1A is a diagram showing the domain used to generate anti-PS1 antibodies. The sequence of the amino-terminal region of PS1 contained within the glutathione S-transferase fusion protein (GSTPS1/NT) is shown under a model of PS1 indicating the approximate locations of the seven potential transmembrane-spanning domains (SEQ ID NO:1). Below this is the sequence of the three peptides (SEQ ID NOS:2,3, and 4)used to characterize the NT1 monoclonal antibody; the sequence containing the NT1 epitope is boxed.

Table 1 shows the levels of presenilin-1 immunoreactivity in ventricular cerebrospinal fluid (CSF) from Alzheimer patients and unaffected individuals. Values given are immunoreactivity (see Detailed Description) of presenilin-1 present in 50 $\mu$l (30–50 $\mu$g of total protein) of ventricular CSF obtained from Brain Tissue Resource Center, McLean Hospital, Belmont, Mass. and National Neurological Research Specimen Bank, Los Angeles, Calif.

DETAILED DESCRIPTION

I. Generation of Antibodies Against Presenilin-1

Useful antigens

The antigens used for generating anti-PS1 antibodies may be PS1, or a fragment that may be 8–50 amino acids in length and contains more than 90% sequence identity with the corresponding region of the native PS1 protein. Preferably, the PS1 fragment used for antibody generation is located within the first 100 amino acids starting from the amino terminus, which contains the amino acid sequence RRSLGHPEP (SEQ ID NO:9). The N-terminal region of PS1 contains the most concentrated primary sequence divergence between human and mouse PS1, as well as between PS1 and its homologue, PS2 (see Examples). A monoclonal antibody raised against this region has proven to be highly specific for PS1 and is preferred for PS1 analysis (NT1, see Examples).

All anti-presenilin-1 antibodies mentioned herein refer to antibodies that are capable of specifically binding at least one of the above described antigens.

Methods for generating monoclonal antibodies

The hybrid cell lines of the invention may be produced by various methods generally known to those of ordinary skill in the art (Harlow et al., Antibodies, A Laboratory Manual, Cold Spring Harbor Laboratory Press, Cold Spring Harbor, N.Y.). In general, the method involves immunizing suitable mammals (such as mice) with the antigens of interest, fusing antibody producing cells isolated from the spleen of the animal with myeloma cells, cloning the resulting hybrid cells, and selecting those cells which produce the desired monoclonal antibody which binds the antigen of interest.

Immunizations are usually performed with purified antigens. The usual mammals used for immunizations are mice, especially CD-1 mice, but other mammals and mouse strains may also be employed. The immunizations are performed in a manner known in the art, such as by administering intraperitoneally, intravenously and/or subcutaneously three to six injections each containing an appropriate amount of purified antigen (i.e., from about 1 mg to about 50 mg) at intervals of about one to six weeks, usually together with an adjuvant that stimulates the production of lymphocytes, e.g., complete or incomplete Freund's adjuvant.

Antibody producing cells present in the spleen of the immunized animals are taken from the animal two to six days after the last ("booster") immunization and fused with myeloma cells of a suitable cell line. Myeloma cell lines and cell lines derived therefrom are known as suitable fusion partners. The myeloma cell line is generally derived from the same species as the immunized mammal, since intra-species hybrids are more viable than inter-species hybrids.

Myeloma cells that lack the enzyme hypoxanthine-guaninephosphoribosyl transferase (HGPRT) or the enzyme thymidine kinase (TK) and which do not survive in a selective culture medium containing hypoxanthine, aminopterin and thymidine (HAT medium), can be employed. Myeloma cells and cell lines prepared therefrom that do not survive in HAT medium and do not secrete any immunoglobulins or parts thereof, for example, the cell line XS63, can also be used (XS63 cells are available from the American Type Culture Collection, Rockville, Md., ATCC# TIB 17). Various fusion-promoters, for example, Sendai virus or other paramyxoviruses, optionally in UV-inactivated form, calcium ions, surface-active lipids, such as isolecithin, or polyethylene glycol ("PEG") may also be employed. Myeloma cells are usually fused with a three-to twenty-fold excess of spleen cells from immunized animals in a solution containing from about 30 to 50% PEG having a molecular weight of about 1000 to 4000 daltons. Exposure to PEG for about 2 to 3 minutes appears to be optimal to prevent toxicity to the cells; temperatures of about 37° C., are recommended. After fusion the cells are partitioned out and cultured in selective HAT medium.

Suitable culture media for the growth of the hybrid cells are customary standard culture media, for example, RPM1 Medium or medium containing 20% fetal calf serum which is supplemented with antibiotics. At the beginning of cell growth, so-called feeder cells (e.g., normal mouse peritoneal exudate cells, spleen cells, bone marrow macrophages or the like) can be added. At regular intervals, the culture media may be supplemented by selective HAT medium to prevent hybrid cells from being overgrown by ordinary myeloma cells.

The cell culture supernatants of the hybrid cells surviving HAT selection are examined for the presence of the desired monoclonal antibodies. Advantageously, the cell supernatants can be tested in a standard immunoassay, e.g., Western blot analysis, that demonstrates the binding of monoclonal antibodies to the antigen of interest.

Those hybridomas can be subsequently screened for desired specificity as well as other desirable characteristics such as thermostability. The screening methods include Western blot analysis and ELISA, which are known to those of ordinary skill in the art. The desired hybridoma cell lines can be maintained as viable cultures and/or frozen for storage.

Large quantities of the desired monoclonal antibodies can also be obtained by multiplying the hybridoma cells in vivo. For this purpose, antibody producing hybridomas are inoculated intraperitoneally into syngenic mammals, and after 1 to 3 weeks, the antibodies are isolated from ascites fluid of those mammals. For example, hybrid cells originating from CD-1 mice can be injected intraperitonealiy into CD-1 mice that have previously been pretreated intraperitoneally with a hydrocarbon such as 2, 6, 10, 14-tetramethylpentadecane (pristane) to prevent fluid drainage from the intraperitoneal cavity, and after 8 to 10 days, ascites fluid is taken from these animals.

The present invention encompasses all monoclonal antibodies exhibiting the characteristics of the antibodies described herein. In other words, antibodies that bind presenilin-1 specifically are within the scope of the invention regardless of the immunoglobulin class or subclass to which they belong. For example, a monoclonal antibody exhibiting the characteristics described herein may be of class IgG1, IgGa, IgGb, IgG3, or of classes IgM, IgA, or of other known Ig classes. Furthermore, while a hybrid cell line generated from a known mouse myeloma and spleen cells from a known species of immunized mouse cannot be further identified except by reference to the antibody produced by that specific hybrid cell line, all hybrid cell lines producing antibodies having the reactivity characteristics described above are within the present invention.

Methods for generating polyclonal antibodies

The polyclonal antibodies of the invention may be produced by various methods generally known to those of ordinary skill in the art (Sambrook et al., Molecular Cloning, A Laboratory Manual, 2nd edn., Cold Spring Harbor Laboratory Press, Cold Spring Harbor, N.Y.; Harlow et al., Antibodies, A Laboratory Manual, Cold Spring Harbor Laboratory Press, Cold Spring Harbor, N.Y.). In general, the methods involve immunizing suitable mammals with the antigen of interest, bleeding the mammals, and preparation of antiserum from the mammal's blood. Immunizations are usually performed with purified antigens. The usual mammals used for immunizations are rabbits, but other mammals including goats and mice may also be employed. Antigens are injected via popliteal lymph nodes, intradermally, subcutaneously, or into a single intramuscular site.

Although the immunization schedule will vary according to the nature of the antigen, the amount of antigen available, the immunogenicity of the antigen, and the mammal used, a reasonable schedule for a rabbit is as follows. One hundred $\mu$g of antigen is dissolved in 0.5 ml of a buffer in which the antigen is soluble, and the solution is emulsified with an equal volume of Freund's complete adjuvant. One-half ml of emulsified antigen-adjuvant is injected into each of two limbs of the animal and 4–6 weeks later, 0.25 ml of the emulsified antigen-adjuvant is injected into another limb. Twenty-40 ml of blood should be drawn 7–10 days after each booster injection, serum prepared, and tested for the presence of the antibody by standard methods (ELISA, Western, RIA, or immunoprecipitation). Animals that have responded can be boosted at regular intervals until a high titer of antibody is attained. Blood (40 ml) then can be withdrawn weekly until the titer drops.

In order to prepare the antiserum, blood is collected from animals that have been fasted for several hours and then allowed to clot at room temperature. A glass rod or sealed pasteur pipet is then used to "ring" the clot. During the next several hours the clot will retract to about half its original volume, leaving the antiserum as a straw-colored liquid. The antiserum is then transferred to a fresh tube and the clot centrifuged at 1500 g for 10 minutes at room temperature. The supernatant is combined with the previously removed antiserum, the clot discarded, and the antiserum stored as either a lyophilized powder, at −20° C., −70° C. or at 4° C. in the presence of 0.02% sodium azide.

Both the monoclonal and polyclonal antibodies produced in vitro or in vivo may be purified using various methods, for example, affinity chromatography, gel filtration chromatography, ion-exchange chromatography or DEAE-cellulose chromatography. Optionally, selected proteins in the culture supernatants or ascites fluid, including the desired antibodies, may be precipitated using specific concentrations of ammonium sulphate or the like before being subjected to chromatography.

II. Analysis of the Expression and Processing of Presenilin-1 by Immunoassays

The amount of PS1 expressed in cells can be examined by immunoassays. These assays measure the amount of binding between PS1 and an anti-PS1 antibody by the use of enzymatic, chromodynamic, radioactive, or luminescent labels that are attached to either the anti-PS1 antibody or a secondary antibody which binds the anti-PS1 antibody. The immunoassays include, but are not limited to, Western and dot blot analyses, immunoprecipitation, and immunocytochemical staining, all of which are techniques known to those of ordinary skill in the art (Harlow et al., Antibodies, A Laboratory Manual, Cold Spring Harbor Laboratory Press, Cold Spring Harbor, N.Y.). Additionally, if the amount of presenilin-1 in body fluid, e.g., cerebrospinal fluid, is to be examined, ELISA may also be performed (Harlow et al., Antibodies, A Laboratory Manual, Cold Spring Harbor Laboratory Press, Cold Spring Harbor, N.Y.). However, one advantage Western blot analysis may have over the other techniques is that it reveals conveniently the in vivo processing pattern of presenilin-1. It has been shown that presenilin-1 is processed, in a tissue-specific manner, to yield smaller isoforms (see Examples).

III. Analysis of Presenilin-1 in Cerebrospinal Fluid

Techniques for collecting cerebrospinal fluid (CSF) are well known in the art (see, e.g., Appleyard et al., 1987, Brain 110: 1309; and Wester et al., 1990, J. Neurochem. 54: 1148). In the present example, CSF was collected from the lateral ventricular of the brain using a 16-gauge spinal needle within 24 hours after death. Cellular debris in the sample was removed by centrifuge at 15,000×g. Lumbar CSF can be isolated by the use of a similar technique (see, e.g., The Merck Manual, 1746–1748, 12th edition, D. N. Holvey, ed., Merck, Sharp, and Dohne Research Publishing, New Jersey, 1972). Analysis of lumbar CSF is particularly useful, as the sample can be obtained from a living patient.

The CSF sample can be examined by aforementioned immunoassays for the amount and isoformal profile of PS1. In the present example, whose data are shown in Table 1, presenilin-1 in ventricular CSF is quantified by Western blot analysis using the NT1 monoclonal antibody (Schwager et al., Journal of Neurochemistry 64: 443, 1995; see Examples).

IV. Use of Anti-PS1 Antibodies for Diagnosis of Alzheimer's Disease

Anti-presenilin-1 antibodies can be used to diagnose Alzheimer's disease. As demonstrated in Table 1, the level of PS1 in CSF from Alzheimer's patients is substantially lower than normal. Therefore, one of ordinary skill in the art can analyze, by an immunoassay, the PS1 level in lumbar cerebrospinal fluid from patients; and a significant decrease (at least 50%, or preferably 200%) of the PS1 level indicates Alzheimer's disease. In addition, one can perform a postmortem diagnosis of Alzheimer's disease by analyzing the PS1 level in ventricular CSF from a patient.

The above described diagnosis can be facilitated by the use of kits which contain the reagents required for carrying out the assays.

V. Identification of Potential Alzheimer's Therapeutics

The present invention provides methods for identifying potential Alzheimer's therapeutics. The effectiveness of a candidate compound can be indicated by its ability to restore significantly the presenilin-1 level in CSF of AD patients. The compounds can be administered to the patient by any appropriate method suitable for the particular compound, e.g., orally, intravenously, parentally, transdermally, or transmucosally. Therapeutic doses are determined specifically for each compound, most administered within the range of 0.001–100.0 mg/kg body weight, or within a range that is clinically determined as appropriate by those skilled in the art.

VI. Use of Retinoblastoma Cells for Studying Presenilin-1

Smaller processed forms of PS1 predominate in human and primate tissues (see Examples). The brain is unique among various tissues in the complexity of the processed forms, in terms of numbers and size heterogeneity. As demonstrated by Western blot analysis (FIG. 2 and 4C), four different human cell lines displayed processing patterns similar to those of non-neural tissues. Only the Y79 human retinoblastoma cell line displayed a complexity similar to that seen in human brain, implying that the proteolytic processing mechanisms be similar. Because proteolytic processing appears to be a key aspect of PS1 function, and many of the presenilin mutations that cause familial Alzheimer' disease are located within the region where processing is likely to occur, it is crucial to understand the molecular mechanisms underlying PS1 processing. The resemblance in PS1 processing between Y79 and brain makes Y79 (and likely other similar retinoblastoma cells or lineage-related cells) an excellent model for studying the function and regulation of PS1 in brain.

Several primate retinoblastoma cell lines can be obtained from the American Type Culture Collection (Maryland). Particularly, the Y79 human retinoblastoma cells can be grown in suspension in Dulbecco's modified Eagles's medium (DMEM) containing 10% fetal bovine serum, 2 mM glutamine in a humidified atmosphere containing 5% $CO_2$.

The following examples are meant to illustrate, but not limit, the methods and compositions of the present invention. Other suitable modifications and adaptations of the variety of conditions and parameters normally encountered in immunodiagnostics which are obvious to those skilled in the art are within the spirit and scope of the present invention.

EXAMPLES: EXPERIMENTAL DATA

Materials and Methods cDNAs and transfections.

The coding region of PS1 was amplified by PCR from a human liver cDNA library (Clontech) using the oligonucleotides 5'-TCACATCGGAAACAAAACAG (SEQ ID NO:5) and 5'-GCGAATTCGTCGACACCTCGTCCCTCAAATCT (SEQ ID NO:6) and cloned blunt/EcoRI into the vector pBluescript. The fidelity of the PCR was confirmed against the previously published sequence (Sherrington et al., Nature, 375: 754, 1995). After transfer to the mammalian expression vector pCDNA3 (Invitrogen), murine Ltk-cells (Kit et al, Exp. Cell Res., 31: 297) were transfected by lipid micelle (lipofectin, Gibco/BRL) and stable transfectants selected in 400 µg/ml G418 (Gibco/BRL). Treatment with 20 mM sodium butyrate (Sigma) for two days (Mathews et al., 1992) was found to be necessary to detect PS1 expression. Multiple independent clones showing similar patterns of immunofluorescence labeling were identified; the line used in this study (L/PS1 cells) was further subjected to limiting dilution subcloning.

In addition to the L cells, the non-adherent human myelogenous leukemia cell line K-562 was transfected with the human PS1 construct. A population of G418 resistant K-526 cells was established; limiting dilution subcloning yielded a clonal line overexpressing PS1.

Antibodies.

A PCR generated cDNA fragment encoding 47 amino acid residues of the N-terminal region of PS1 (see FIG. 1; the oligonucleotides used were 5'-CGGGATCCCACCTGAGCAATACTGTACG (SEQ ID NO:7) and 5'-CGAATTCCTCATCTTGCTCCACCAC) (SEQ ID NO:8) was cloned BamHI/EcoRI into pGEX2T (Pharmacia) to yield a glutathione S-transferase fusion protein construct (GST-PS1/NT). After bacterial expression and purification, GST-PS1/NT was used to immunize rabbits and Balb/c mice. Hybridomas were generated by fusing spleen cells with Sp2/0-Ag14 and initially screened by ELISA against GST-PS1/NT and also against the synthetic peptides described in FIG. 1.

Cell lines, immunofluorescence labeling, and metabolic labeling.

All cell lines were maintained in DMEM supplemented with 10% FBS, penicillin, streptomycin, and glutamine. Ltk-cells were a gift of Dr. Douglas M. Fambrough, Johns Hopkins University, and the SH-SY5Y a gift of Dr. June Biedler (Biedler et al., 1973); all other cell lines were obtained from the American Type Culture Collection.

For immunofluorescence labeling, L cells were plated onto glass coverslips and allowed to settle overnight. The growth medium was replaced with media containing 20 mM sodium butyrate and, after 2 days of incubation, the cells were fixed by extraction in 100% methanol. NT1 was bound overnight (1 µg/ml) followed by incubation with FITC-coupled secondary antibody (Cappel). Labeling was detected using epifluorescence on a Zeiss microscope fitted with a fluoroscein filter.

Protein Extraction and Western blot analysis.

Cell pellets (K562) or cells grown on plastic (all other cell lines analyzed) were directly extracted in 4.8% SDS, 2 M urea, 8% sucrose containing protease inhibitors, and DNA was sheared by passing through progressively smaller-diameter syringe needles.

Frozen postmortem brain tissue from the prefrontal cortex (Brodmann area 10) of 14 individuals with the probable clinical diagnosis of Alzheimer's disease and 9 age-matched (AD: 76±3.8 years; control: 69±4.2 years; expressed as mean ±SE), neurologically normal controls was procured from the Harvard Brain Tissue Resource Center at McLean Hospital. For the former group, diagnosis of definite Alzheimer's disease was established neuropathologically by CERAD criteria; control cases exhibited no diagnostic neuropathology. One-half gram of gray matter was homogenized in 250 mM sucrose, 1 mM EDTA, 1 mM EGTA, 20 mM Tris (pH 7.4) followed by centrifugation for 1 hour at 100,000 g. The membrane pellet was extracted in 4.8% SDS, 2 M urea, 8% sucrose, and the DNA sheared. PS1 was fully recovered in the membrane fraction and not detectable in the supernatant (data not shown).

The monkey tissues used in this study were kindly supplied by Drs. Terrence W. Deacon and Ole Isacson. Tissues were obtained from an adult male *Macaca fascicularis* immediately after sacrifice and were frozen in isopentane/liquid nitrogen. With the exception of brain, the tissues were first disassociated using a polytron; otherwise, membrane proteins were prepared as for human brain.

For Western blot analysis, samples were heated to 56° C. for 10 minutes in 4.8% SDS, 2 M urea, 8% sucrose, 350 mM 2 mercaptoethanol and loaded onto discontinuous SDS-polyacrylamide gels. Including 2 M urea in both the stacking and 10% acrylamide resolving gels was found to improve PS1 resolution. Proteins were transferred to Immobilon-P membranes (Millipore) and after incubating overnight in binding solution (PBS/5% milk containing 5 µg/ml NT1) PS1 was detected by incubating with either alkaline phosphatase-coupled secondary antibody followed by NBT/BCIP (both Promega), or with HRP-coupled secondary antibody (Cappel) followed by ECL (Amersham). For the competition assays shown in FIG. 4B, synthetic peptides were added to the binding solution (4:1 peptide:antibody molar ratio) and this mixture was pre-incubated overnight at 4° C. prior to being used for Western blot analysis.

Results

Antibodies and detection of PS1 in transfected L cells.

We have generated antibodies against PS1 to study its expression both in vivo and within in vitro cell systems. Antibodies were raised against a GST fusion protein containing 47 amino acid residues from the amino-terminus of human PS1 (GST-PS1/NT; FIG. 1A). With the initial objective of producing human PS1-specific antibodies, we chose this region because it contains the most concentrated primary sequence divergence between human and mouse PS1 (Sherrington et al., 1995) and because PS1 and PS2 show little sequence conservation amino-terminal to the first potential transmembrane span (Sherrington et al., Nature, 375: 754, 1995; Levy-Lahad et al., Science, 269: 973, 1995; li et al, Proc. Natl. Acad. Sci. USA, 92: 12180, 1995; Rogaev et al., Nature, 376: 775, 1995).

Figure 1B:
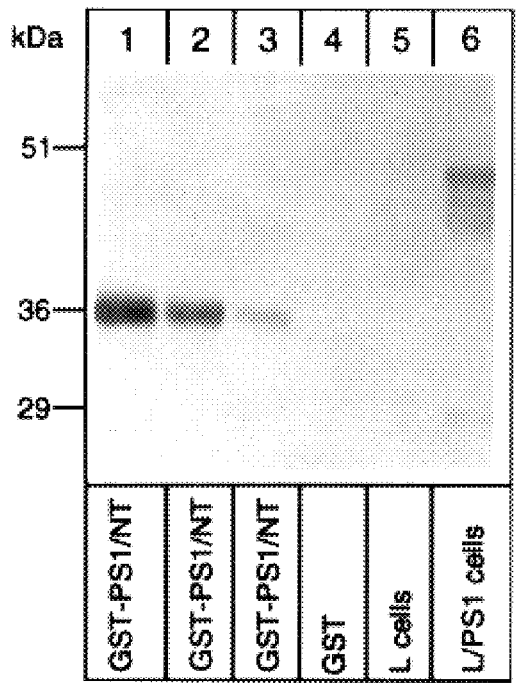
FIG. 1B is a Western blot demonstrating the specificity of the NT1 monoclonal antibody. Purified bacterially produced proteins or total cellular proteins were sized by SDS-PAGE, transferred to a PVDF membrane, and probed with NT1. The following were loaded onto the gel: 50, 20, and 2 $\mu$g GST-PS1/NT (lanes 1 through 3); 100 $\mu$g GST (lane 4); 50 $\mu$g of total protein extracted from murine L cells (lane 5); and 50 $\mu$g of total protein extracted from an L cell line stable transfected with human PS1 (L/PS1 cells; lane 6).

A monoclonal antibody (NT1) was generated that quantitatively recognized GST-PS1/NT by Western blot analysis (FIG. 1B, lanes 1–3) and failed to recognize the GST carrier protein alone (lane 4). Additionally, NT1 bound equally well by ELISA two overlapping, synthetic peptides from within the amino-terminus of PS1 (peptides B and C) while failing to recognize a third (peptide A), indicating that the epitope recognized by NT1 is contained within the sequence RRSLGHPEP (SEQ ID NO:9). This sequence diverges from mouse PS1 (RQRLDNPEP; SEQ ID NO:10) and shows no homology to human PS2. Consistent with these data, NT1 failed to recognize by Western blot analysis any protein expressed by a mouse cell line (the fibroblast-like L cell; FIG. 1B. lane 5) but detected a group of proteins migrating between 46 and 42 kDa, close to the predicted molecular weight for PS1 of 52 kDa, when the human PS1 cDNA was expressed after transfection of the same line (L/PS1 cells; lane 6). In addition to this dominant protein, two smaller proteins ($M_r$ ~28 kDa) was also detected. Rabbit antisera raised against GST-PS1/NT revealed the same bands by Western blot analysis of L/PS1 cell extracts, although detection with these antibodies was weaker (data not shown).

Figure 1C:
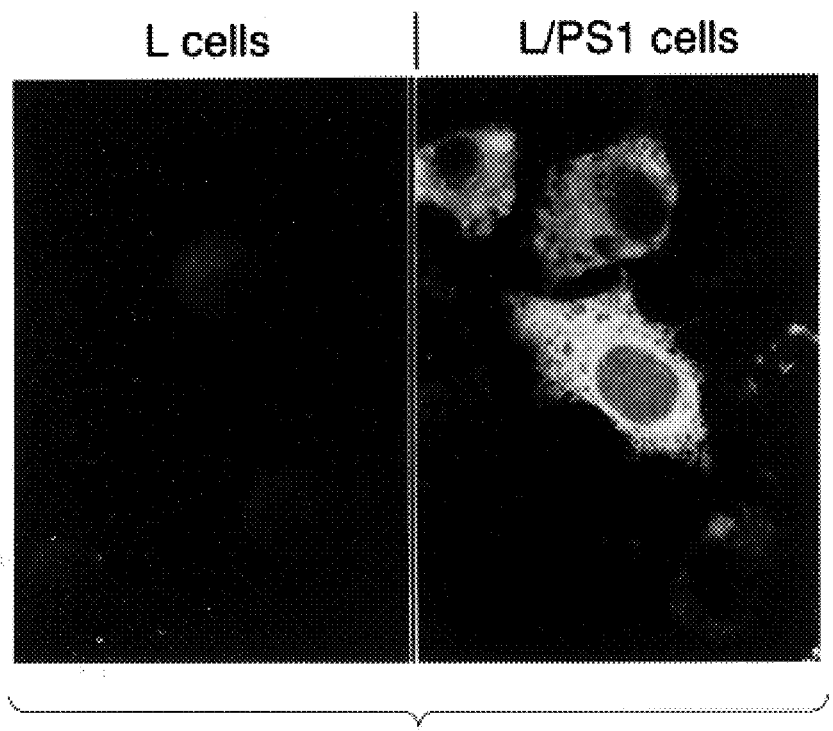
FIG. 1C is a photograph showing immunofluorescence labeling of L cells expressing human PS1. L cells (right panel) or L/PS1 cells (right panel) grown on glass coverslips were fixed and labeled with the NT1 mAb as described in Detailed Description.

The specificity of the amino-terminal PS1 antibody is further demonstrated in FIG. 1C, in which parental L cells and L/PS1 cells were analyzed by immunofluorescence labeling. While L cells failed to label with NT1 (left panel), L/PS1 cells were strongly labeled (right panel). The pattern of an intracellular network and a nuclear ring suggestive of an ER localization is consistent with the intracellular localization previously reported (Kovacs et al., 1996, Moussaoui et al., 1996).

Figure 2:
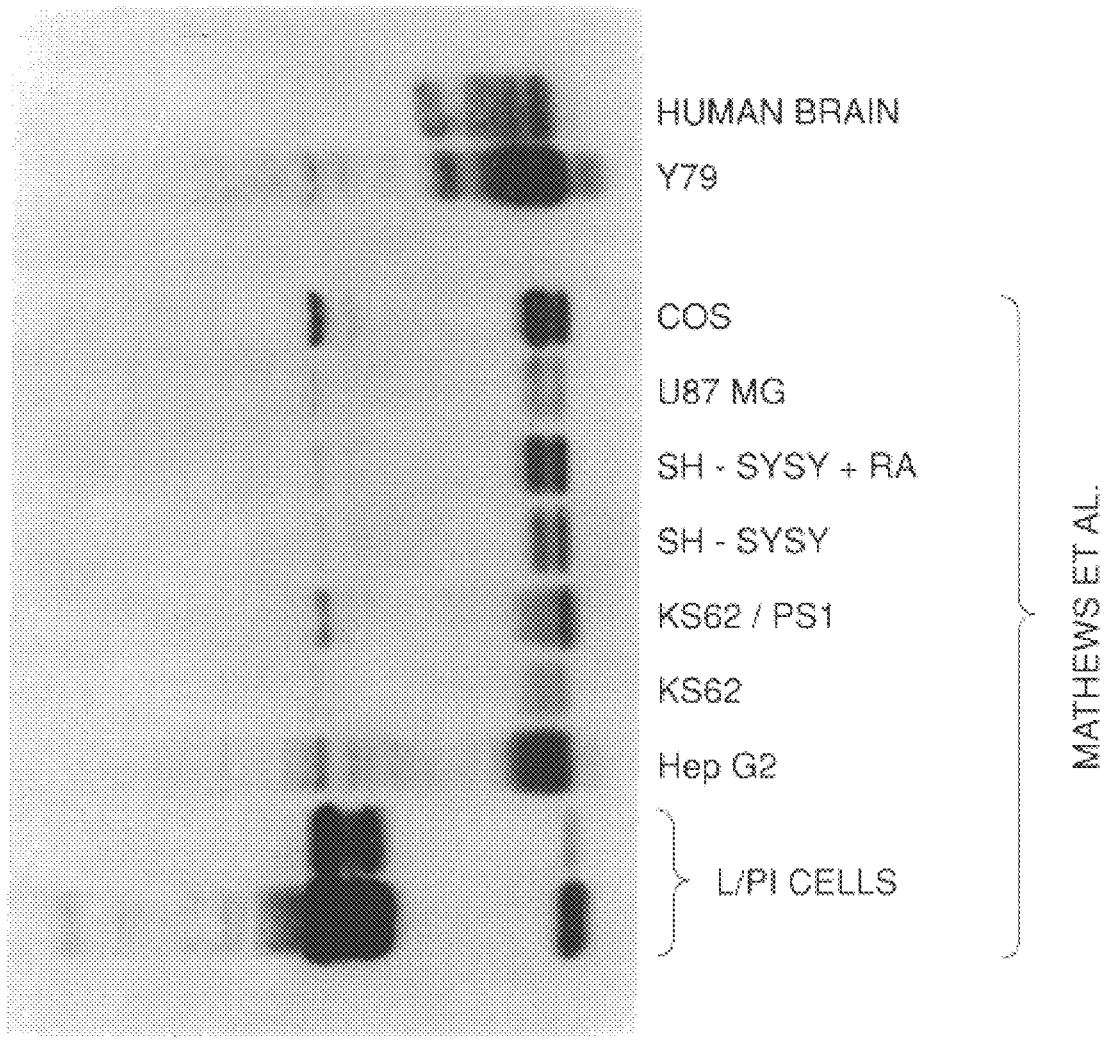
FIG. 2 is a Western blot showing the expression of PS1 in a series of culture cell lines. Total protein was extracted from these cells and was analyzed by use of the NT1 mAb. 100 $\mu$g of protein (with the exception of lane 2) was loaded on the gel from the following cell lines: L-PS1 (lane 1); 20 $\mu$g L-PS1 (lane 2); Hep G2, a human hepatocellular carcinoma line (lane 3); K-562, a human myelogenous leukemia line (lane 4); K-562 transfected with PS1 (see Methods; lane 5); SH-SY5Y, a human neuroblastoma line (lane 6); SH-SY5Y treated with 10 $\mu$g transretinoic acid for 7 days prior to extraction (lane 7); U87 MG, a human astrocytoma line (lane 8); COS-1, established from African green monkey kidney cells (lane 9); Y79, a human retinoblastoma cell line (lane 11); and human brain (lane 12).

Expression of PS1 in human cell lines. Having demonstrated the specificity of the NT1 mAb in the transfected cells, we used Western blot analysis to detect endogenous PS1 in cell lines as a prelude to investigating its properties in human brain (FIG. 2). While the pattern of a 46 kDa band and a cluster of bands near 28 kDa detected from four human cell lines and one monkey cell line is similar to that seen from L/PS1 cells (compare lanes 1 and 2 with lanes 3–9), the relative intensities of these bands are quite different. Although a 46 kDa form of endogenous PS1 could be detected, the vast majority of NT1 immunoreactivity from the primate cell lines was associated with smaller protein species clustered between 30 and 28 kDa. Overexpression of human PS1 in K-562 cells significantly increased the level of the both 46 kDa band and the 30–28 kDa cluster of bands (compare lanes 4 and 5). K-562 cells were found not to tolerate butyrate treatment, thus precluding the high level of PS1 overexpression obtained following butyrate-induction in the L cells. Retinoic acid-induced neuronal differentiation of SH-SY5Y cells (Pahlman et al., 1984) also led to an increase in levels of the 46 kDa band and an even greater increase in the 30–28 kDa cluster of bands (compare lane 6 with 7). Finally, the COS cells shown in lane 8 demonstrate that the NT1 mAb crossreacts with monkey PS1.

Figure 3A:
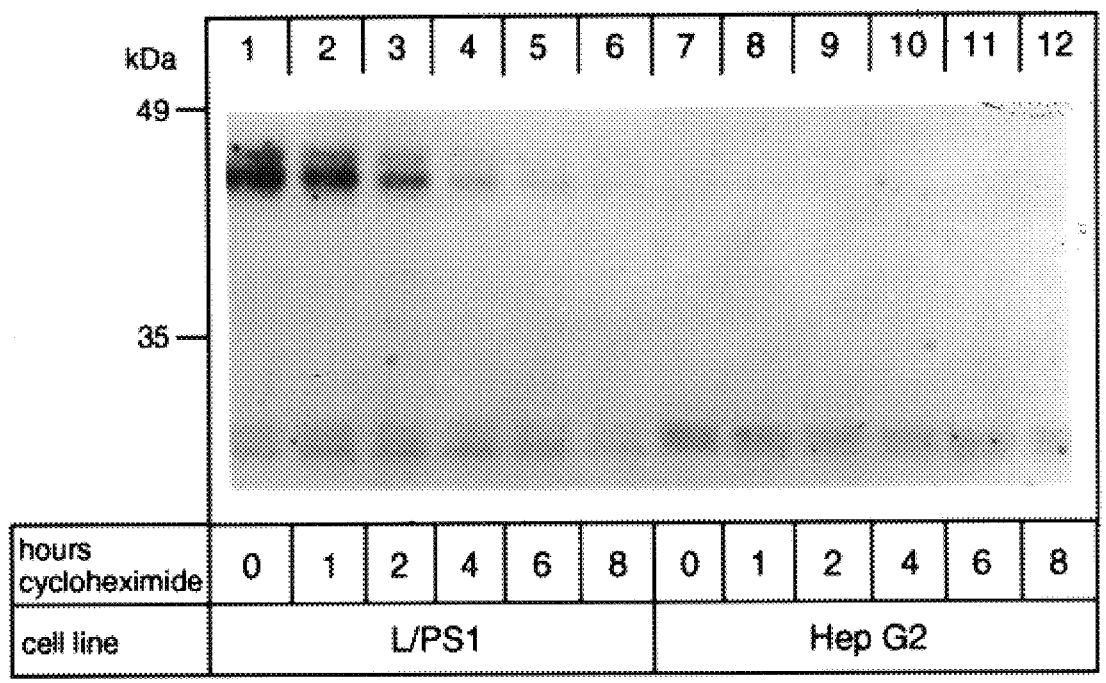
FIG. 3A is a Western blot showing the turnover of PS1 after inhibition of protein synthesis. Equal numbers of L/PS1 cells (lanes 1–6) or Hep G2 cells (lanes 7–12) were seeded into 6-well clusters. Two days after butyrate-induction of the L/PS1 cells, 75 $\mu$g/ml cycloheximide was added for the indicated times. Protein extraction and Western blot analysis with NT1 was as described in Detailed Description.
Figure 3B:
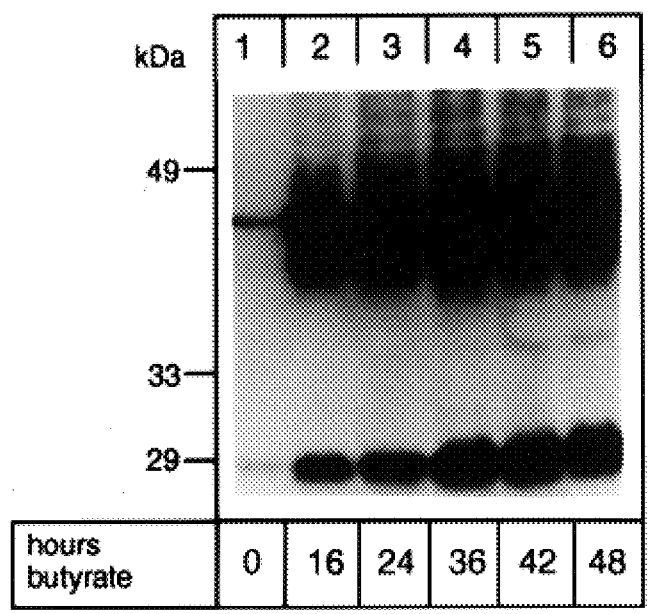
FIG. 3B is a Western analysis showing the induction of PS1 expression in L/PS1 cells by butyrate treatment. Equal numbers of L/PS1 were seeded as above and treated with 10 mM butyrate for the indicated times. Extraction and Western blot analysis with NT1 was as described in Detailed Description.
Figure 3C:
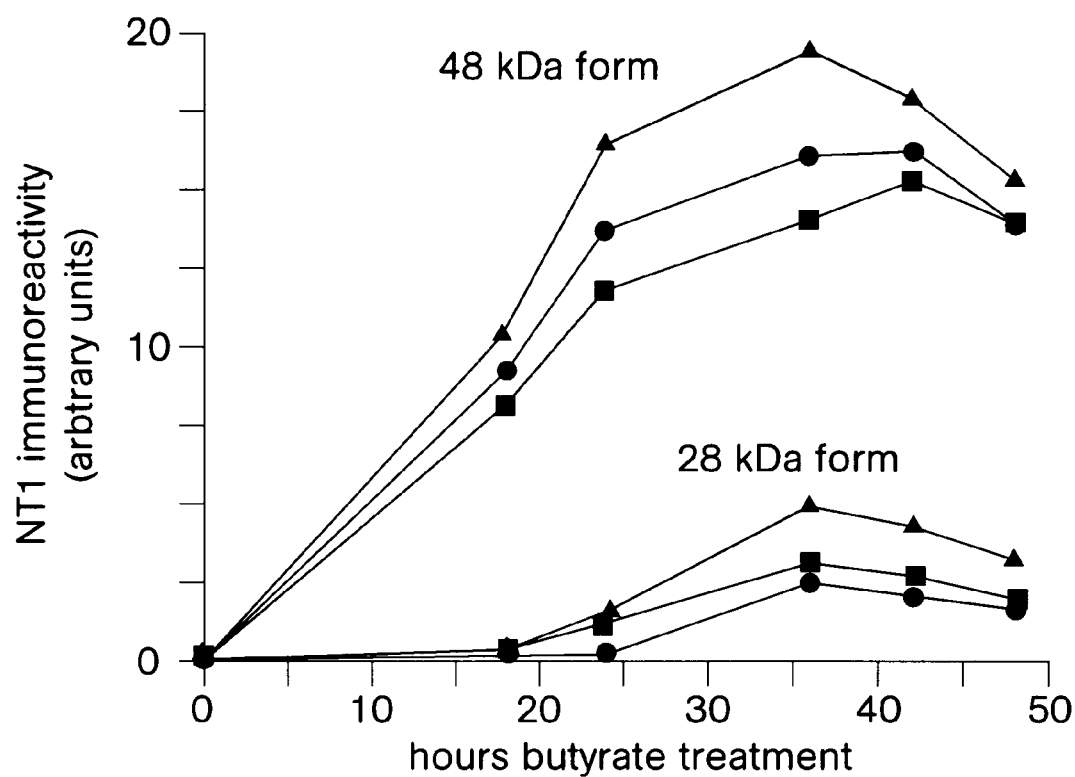
FIG. 3C is a graph showing the quantitation of PS1 levels after butyrate induction. The data from the experiment shown in FIG. 3B and two additional experiments are included.

Processing of PS1 occurs in vivo. One possible explanation for the smaller forms of PS1 seen in FIG. 2 would be proteolysis of the protein following cell extraction. While the markedly different ratios of the 46 kDa form to the smaller forms in transfected L cells versus the primate cell lines suggests that this is not the case, we sought to demonstrate that both forms exist in vivo. In FIG. 3A, L/PS1 and Hep G2 cells were treated with cycloheximide and the forms of PS1 present after the cessation of protein synthesis were determined by Western blot analysis. Without treatment, PS1 expressed in the L cells resolved into a doublet at ~46 kDa and a minor doublet at ~28 kDa (lane 1). A significant reduction in the 46 kDa doublet occurred within 1 hour of cycloheximide addition (lane 2). The level of the 46 kDa form continued to decline with longer treatment (lanes 3–6) and, after 8 hours, little of this protein remained (lane 6). In contrast, cycloheximide treatment of up to 8 hours had relatively little effect on the abundance of the 28 kDa form of the protein (compare lane 1 with lanes 2–6). Indeed, after 8 hours of protein synthesis inhibition, the NT1 labeling seen from the L/PS1 cells was very similar to that seen from Hep G2 cells without cycloheximide treatment (lane 7). Like the L/PS1 cells, the ~28 kDa doublet seen in Hep G2 cells decreased only slightly during 8 hours of cycloheximide treatment. The relative stability of the 28 kDa form precludes it being the result of post-extraction proteolysis of the more rapidly-turning over 46 kDa form, but is consistent with in vivo processing of the 46 kDa form to yield the 28 kDa form. While metabolic labeling followed by chase and immunoprecipitation might directly demonstrate a precursor role for the 46 kDa form of PS1, several factors prevented us from obtaining these data. First, our anti-PS1 antibodies immunoprecipitate poorly. Second, in cells overexpressing PS1 the amount of the synthesized protein appearing as 28 kDa processed forms is low, and therefore difficult to detect and quantify in radioactive form. Similarly, in cells expressing endogenous levels of PS1, PS1 labeling is exceedingly low.

Expression and processing of PS1 in brain and other tisues

Figure 4A:
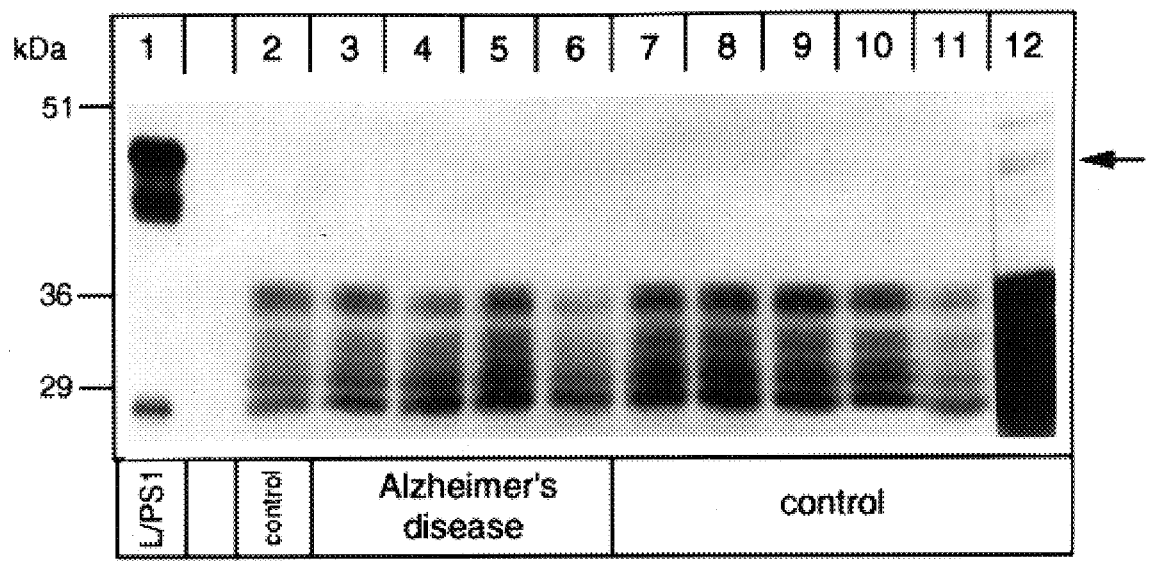
FIG. 4A is a Western blot for analysis of PS1 from human brain. Membrane pellets were prepared from human pre-frontal cortex as described in Detailed Description. 200 $\mu$g of protein was sized by SDS-PAGE, transferred to PVDF membrane, and PS1 detected using the NT1 mAb. As a reference, 50 $\mu$g of total protein from L/PS1 cells was loaded in lane 1. Lanes 3 through 6 consist of material from individuals with the diagnosis of Alzheimer's disease, whereas lanes 2 and 7 through 12 are from age-matched controls. Lane 13 is a longer exposure of lane 12 showing the 46 kDa doublet.
Figure 4B:
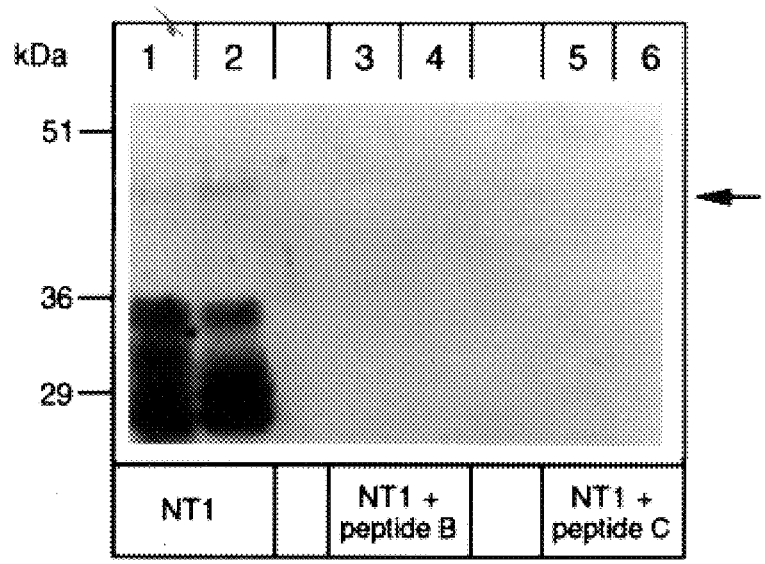
FIG. 4B is a Western blot demonstrating the competition of peptides B and C for the binding of NT1 to human and monkey brains. The Western blot analysis was done as above using 200 $\mu$g of protein extracted from a membrane pellet prepared from human brain (lanes 1, 3, and 5; a control case) and monkey brain (lanes 2, 4, and 6). Lanes 1 and 2 were probed with NT1; lanes 3 and 4, NT1 with the addition of peptide B.; lanes 5 and 6, NT1 with the addition of peptide C (see Detailed Description and FIG. 1 for details).

Next, we examined PS1 from human brain (FIG. 4A). PS1 expression and processing in prefrontal cortex from fourteen individuals diagnosed with late-onset, sporadic AD (four cases depicted in lanes 3–6) were compared to that from nine age-matched neurologically normal controls (seven cases shown in lanes 2, 7–11) by Western blot analysis. Both the level of PS1 expression and type of processing were found to be remarkably similar among individuals within each group and between the AD and control groups. Quantitation of the total PS1 immunoreactivity from control vs. AD cases confirmed this interpretation (control: 1.00±0.04; AD: 0.91±0.05; p>0.1; expressed as mean ±SE, normalized to control value). As seen in the case of endogenous PS1 expressed in cell lines, processed forms of PS1 greatly predominated. Nevertheless, a faint 46 kDa doublet, comigrating with the 46 kDa band detected from L/PS1 cells (compare lane 1 with lane 12), could be detected on immunoblots developed for longer periods. Unlike in the cell lines, however, the processing of PS1 in brain appears to be more complex and results in the generation of multiple bands between 35 and 28 kDa.

A common difficulty encountered when interpreting the expression, processing, and/or degradation of a protein derived from human tissue is the potential for modification of the protein during the post-mortem interval (PMI). Although PMI's between the two groups were closely matched (AD: mean=8.6 hours, range 1.0–13.7 hours; control: mean=9.5 hours, range 1.0–22.8 hours) and the similar electrophoretic patterns argues against large PMI effects, we directly addressed the issue of PMI artifact in the Western blot shown in FIG. 4B. PS1 expression and processing from human brain (PMI=20.5 hours; lane 1) were compared to monkey brain frozen immediately upon sacrifice of the animal (lane 2). The pattern of PS1 observed from human brain was nearly identical to that seen from monkey brain, indicating that PS1 processing occurred in vivo. That NT1 indeed detected PS1 from human and monkey brain is demonstrated by the Western blots probed with this antibody in the presence of peptide B (lanes 3 and 4) and peptide C (lanes 5 and 6), the two peptides previously shown to bind NT1 by ELISA (see FIG. 1). Competition with either peptide effectively eliminated the strong bands between 35 and 28 kDa as well as the faint doublet detected at ~46 kDa.

Figure 4C:
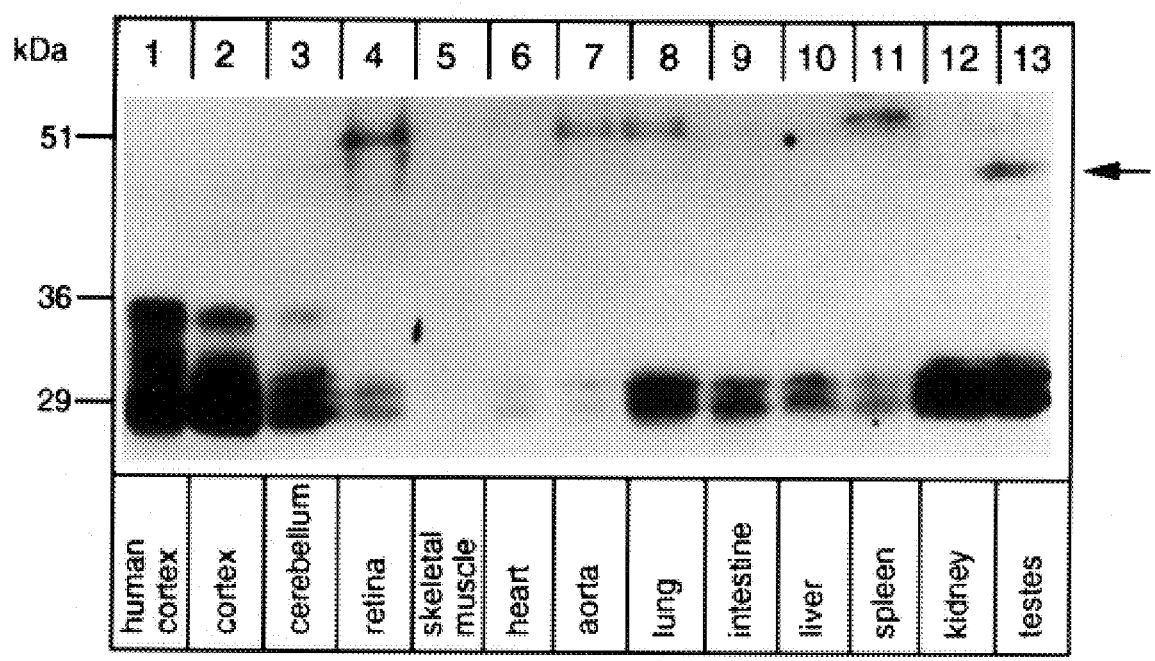
FIG. 4C is a Western blot for analysis of PS1 from neuronal and non-neuronal tissues. 200 $\mu$g of membrane protein prepared from human brain (lane 1) and the indicated monkey tissues (lanes 2 through 12) was analyzed as in A. The 46 kDa full-length form of PS1 is indicated by arrows.

In order to determine whether this complex pattern of PS1 processing is unique to brain, we examined multiple monkey tissues by Western blot (FIG. 4C). Again, human cortex (lane 1) and monkey cortex (lane 2) showed processed forms migrating between 35 and 28 kDa. With the exceptions of cerebellum (lane 3), which showed a pattern similar to cortex, and retina (lane 4), from which a ~35 kDa band could be detected upon longer exposure, the pattern of PS1 processing in the other tissues examined was less complex (lanes 6–13). In these non-neuronal tissues, the majority of PS1 detected by NT1 migrated between 30 and 28 kDa (also detected from skeletal muscle, lane 5, upon longer exposure). In addition to this difference, the level of expression of PS1 was found to be greater in brain than in other tissues, although high levels of PS1 were also detected in lung (lane 8), kidney (lane 12), and testes (lane 13). Finally, the 46 kDa form of PS1, consistently detected from brain (lanes 1–3), was more difficult to demonstrate from non-neuronal tissues, with the notable exception of testes (lane 13). These data on PS1 protein expression are consistent with previous Northern blot analysis detecting PS1 message in all tissues (Sherrington et al., Nature, 375: 754, 1995); however, the unique processing in brain suggests the potential of a specialized role for PS1 in neuronal tissues.

What is claimed is:

1. A method of diagnosing sporadic Alzheimer's disease in a human patient, comprising measuring the level of presenilin-1 present in a biological sample of said patient, and comparing said level of presenilin-1 to normal levels, wherein a decrease in said level relative to normal indicates sporadic Alzheimer's disease.

2. The method of claim 1, wherein said biological sample is lumbar cerebrospinal fluid.

3. The method of claim 1, wherein said biological sample is ventricular cerebrospinal fluid.

4. The method of claim 1, wherein said measuring is by the use of an immunoassay comprising contacting said biological sample with an antibody capable of specifically binding presenilin-1 and measuring the amount of said binding.

5. The method of claim 4, wherein said contacting is by Western blot analysis.

6. The method of claim 4, wherein said contacting is by ELISA.

7. The method of claim 4, wherein said antibody specifically binds to human presenilin-1, or a fragment thereof.

8. The method of claim 4, wherein said antibody specifically binds to the amino terminal region of human presenilin-1.

9. The method of claim 4, wherein said antibody specifically binds to a peptide that contains the amino acid sequence RRSLGHPEP.

* * * * *